(12) United States Patent
Chen et al.

(10) Patent No.: US 12,343,364 B2
(45) Date of Patent: Jul. 1, 2025

(54) LACTOBACILLUS REUTERI GMNL-263 FOR IMPROVING HYPERTENSION AND ITS COMPOSITIONS THEREOF

(71) Applicant: GenMont Biotech Incorporation, Tainan (TW)

(72) Inventors: Yi-Hsing Chen, Tainan (TW); Wan-Hua Tsai, Kaohsiung (TW)

(73) Assignee: GENMONT BIOTECH INCORPORATION, Tainan (TW)

( * ) Notice: Subject to any disclaimer, the term of this patent is extended or adjusted under 35 U.S.C. 154(b) by 570 days.

(21) Appl. No.: 17/552,187

(22) Filed: Dec. 15, 2021

(65) Prior Publication Data
US 2022/0105141 A1 Apr. 7, 2022

Related U.S. Application Data

(63) Continuation-in-part of application No. 16/018,338, filed on Jun. 26, 2018, now abandoned.

(51) Int. Cl.
| | | |
|---|---|---|
| A61K 35/747 | (2015.01) | |
| A61P 9/12 | (2006.01) | |
| C12N 1/20 | (2006.01) | |
| A61K 35/745 | (2015.01) | |

(52) U.S. Cl.
CPC ............ *A61K 35/747* (2013.01); *A61P 9/12* (2018.01); *C12N 1/205* (2021.05); *A61K 35/745* (2013.01)

(58) Field of Classification Search
CPC .................................................... A61K 35/747
See application file for complete search history.

(56) References Cited

U.S. PATENT DOCUMENTS

| | | | | |
|---|---|---|---|---|
| 9,301,984 B2* | 4/2016 | Chen | ............... | A61K 35/745 |
| 2011/0300117 A1* | 12/2011 | Leu | ............... | C12N 1/205 |
| | | | | 435/252.9 |
| 2015/0196608 A1* | 7/2015 | Chen | ............... | A61K 36/06 |
| | | | | 424/93.3 |
| 2015/0238548 A1* | 8/2015 | Huang | ............... | C12N 1/205 |
| | | | | 435/252.9 |
| 2015/0250836 A1* | 9/2015 | Chen | ............... | A23K 10/16 |
| | | | | 424/93.3 |
| 2016/0095889 A1* | 4/2016 | Chen | ............... | A61P 3/06 |
| | | | | 435/252.9 |

FOREIGN PATENT DOCUMENTS

| | | | | | |
|---|---|---|---|---|---|
| GB | 2522188 A | * | 7/2015 | | |
| GB | 2535177 A | * | 8/2016 | ........... | A61K 35/747 |

OTHER PUBLICATIONS

Lee, Seung Won, et al. "Association between changes in systolic blood pressure and incident diabetes in a community-based cohort study in Korea." Hypertension Research 40.7 (2017): 710-716. (Year: 2017).*
Ting et al., Heat Killed Lactobacillus reuteri GMNL-263 Reduces Fibrosis Effects on the Liver and Heart in High Fat Diet-Hamsters via TGF-β Suppression, Int. J. Mol. Sci. 2015, 16, 25881-25896 (Year: 2015).*
Hsieh et al., Heat-killed and live Lactobacillus reuteri GMNL-263 exhibit similar effects on improving metabolic functions in high-fat diet-induced obese rats, Food Funct., 2016, 7, 2374 (Year: 2016).*
Wilde DW, Massey KD, Walker GK, Vollmer A, Grekin RJ. High-fat diet elevates blood pressure and cerebrovascular muscle Ca(2+) current. Hypertension. Mar. 2000;35(3):832-7. doi: 10.1161/01.hyp.35.3.832. PMID: 10720603. (Year: 2000).*
Taylor EB, Ryan MJ. Understanding mechanisms of hypertension in systemic lupus erythematosus. Ther Adv Cardiovasc Dis. Mar. 15, 2016;11(1):20-32. doi: 10.1177/1753944716637807. Epub ahead of print. PMID: 26985016; PMCID: PMC5065379. (Year: 2016).*
Ting, Wei-Jen, et al. "Supplementary heat-killed Lactobacillus reuteri GMNL-263 ameliorates hyperlipidaemic and cardiac apoptosis in high-fat diet-fed hamsters to maintain cardiovascular function." British Journal of Nutrition 114.5 (2015): 706-712. (Year: 2015).*
Healthline Cholesterol Test https://www.healthline.com/health/cholesterol-test (Year: 2012).*
https://www.cdc.gov/bloodpressure/about.htm#print (retrieved Feb. 3, 2024) (Year: 2024).*

* cited by examiner

*Primary Examiner* — Allison M Fox
*Assistant Examiner* — Qing Xu
(74) *Attorney, Agent, or Firm* — WPAT, PC

(57) ABSTRACT

Present invention discloses a *Lactobacillus* composition comprising *Lactobacillus reuteri* GMNL-263 which is a strain of heat-killed dead bacteria and has the effect of lowering blood pressure by inhibition of proinflammatory cytokine IL-1β and enhancement the growth of *Bifidobacterium*, and said *Lactobacillus* composition is a pharmaceutical composition, nutritional supplement, health food or a combination thereof.

5 Claims, 2 Drawing Sheets

A

B

LACTOBACILLUS REUTERI GMNL-263 FOR IMPROVING HYPERTENSION AND ITS COMPOSITIONS THEREOF

BACKGROUND OF THE INVENTION

This application is a continuation-in-part application of U.S. application Ser. No. 16/018,338 filed on Jun. 26, 2018.

FIELD OF THE INVENTION

The present invention relates to probiotic bacterial strains, more particularly to *Lactobacillus* strains, and its composition for improvement of hypertension.

DESCRIPTION OF RELATED ART

Blood pressure is the pressure of blood on the walls of blood vessels generated by contraction and beating of the heart. Circulation of blood through the body is driven by maintaining the blood pressure which consequently helps the transport of nutrients and metabolism of waste. There are two types of blood pressure, systolic blood pressure and diastolic blood pressure, that is, the measurement obtained when cardiac muscle contracts (systole) and relaxes (diastole); normal blood pressure ranges from 90 to 139 mmHg and 60 to 89 mmHg for systolic and diastolic blood pressures, respectively.

Hypertension is a chronic disease caused by elevated blood pressure of arteries and is also a very common chronic disease in the country. Elevated blood pressure will increase the burden of the heart to move circulating blood in blood vessels. Hypertension occurs when the blood pressure is maintained at or higher than 140/90 mmHg. Due to few symptoms, the hypertension is often ignored and usually is identified by screening or when treating other health issues. Some patients may have headache, dizziness, vertigo tinnitus and other symptoms. Once serious, they may even faint or cause internal organs damage. Apart from ignorance of the disease due to unclear symptoms, hypertension is often accompanied by serious complications; the risk of hypertension increases with age and hypertension is an important factor that multiplies the risk of cardiovascular disease. In addition, hypertension is one of the major causes of death resulted from cardiovascular diseases announced by the World Health Organization (WHO). Because hypertension is a chronic disease, the patients must take long-term medication to control their blood pressure which is a heavy expense of time and money.

Hypertension is divided into primary and secondary, in which 90-95% is caused by the primary, that is, no obvious cause; the other accounting for about 5-10% is the secondary, which is caused by other diseases, such as diabetes, kidney disease, endocrine disease, chest and abdomen obesity, thyroid disease, acromegaly or abnormal physiological responses, such as increased production of proinflammatory cytokines (Krishnan et al., 2014) and reduced intestinal probiotic bacteria (Li et al., 2017), etc., are the causes that induce or exacerbate hypertension.

Among them, the chronic type 2 diabetes mellitus (T2DM) is an example of a typical disease associated with hypertension. Because diabetic patients often have symptoms derived from renal artery and systemic arteriosclerosis, which will increase peripheral vascular resistance and systolic pressure resulting in elevated blood pressure. Therefore, patients with T2DM often occur with hypertension which will accelerate vascular damage and consequently cause complications of brain, eye, heart or kidney and other organs, and significantly increase the risk of myocardial infarction and stroke.

Currently, medication is still the major treatment for control of hypertension. However, these patients must take medicine for a long time to maintain their blood pressure, which is not only the heavy burden on time and money, but also the risk of taking medicine carelessly. For example, some medicines may be harmful to pregnant women or fetuses; for patients with diabetes, medication for hypertension may affect blood glucose level and worsen the disease or result in incorrect assessment of the disease condition. In addition, as the mechanism of the medicine itself is different, such as the regulation of cellular receptors, the inhibition of cardiac pulsation or the reduction of neurotransmission, and so on, and have a certain degree of side effects. Hence, searching for other pathways that are effective and without side effects to lower blood pressure is an essential task to solve and prevent the problem of hypertension. There are many studies have focused on how to control and prevent hypertension through health food.

The human body blood pressure regulation system is mainly through the Renin-Angiotensin System (RAS) to ensure blood pressure and the balance of body fluid and electrolyte. In this system, Angiotensin I-Converting Enzyme (ACE) is an important enzyme for the regulation of blood pressure by increasing blood pressure.

Previous studies have shown that the probiotic fermented milk has the effect of regulating blood pressure. Probiotic bacteria can decompose casein through lactose hydrolyzing enzyme and produce unequal amounts of ACE inhibitory peptides; Yamamoto, 1999) to lower blood pressure. Earlier studies also indicated special live bacterial strains can be isolated from the probiotic bacterial strains such as *Lactobacillus helveticus* (*L. helveticus*), *Lactobacillus casei* (*L. casei*), *Lactobacillus rhamnosus* (*L. rhamnosus*), *Lactobacillus acidophilus* (*L. acidophilus*), *Lactobacillus fermentum* (*L. fermentum*), *Lactobacillus bulgaricus* (*L. bulgaricus*) and *Lactobacillus reuteri* (*L. reuteri*) and addition of the bacterial strain(s) and ACE inhibitory peptide to fermented milk can help the bacteria to produce more ACE inhibitory peptides in fermented milk, which has the effect of lowering blood pressure in patients with hypertension (Beltran-Barrientos et al., 2016).

However, this part of the study is limited to some special strains of living bacteria and there are still a number of limitations and deficiencies in the implementation, especially a quite high threshold of both the effective dose of bacteria and the duration required for taking the bacteria. A retrospective study suggested that ingestion of more than $1 \times 10^{11}$ cfu (colony forming unit) of probiotic bacteria per day for at least 8 weeks is required to achieve better blood pressure regulation (Khalesi et al., 2014). In general, the current studies are mostly confined to in vitro or in animal experiments, there are few data on clinical trials on probiotics for lowering blood pressure. The data obtained so far from clinical trials includes the use of fermented milk of mixed bacterial cultures of *L. helveticus* and *Saccharomyces cerevisiae* (*S. cerevisiae*) in patients with hypertension (Hata et al., 1996) or giving normal people with slightly higher blood pressure the fermented milk of *L. helveticus* CM4 (Aihara et al., 2005) and both studies showed the effect of lowering blood pressure; for population at high risk for diabetes, use of the products containing prebiotics and the following bacterial strains: *L. casei, L. acidophilus, L. rhamnosus, L. bulgaricus, Bifidobacterium Breve* (*B.*

Breve), *B. longum* and *Streptococcus* thermophiles (S. thermophiles) all showed an effect of regulation of blood pressure (Mahboobi et al., 2014).

For lowering blood pressure by using probiotics, the use of living bacteria through fermented milk fermentation to produce ACE inhibitory peptides for the control of blood pressure by ingestion is the major pathway. However, because probiotics are not pharmaceutical formulations, but the healthy food type and only limited clinical data is available to support their function, therefore, the efficacy information about the effective dosage and frequency of drinking are often unclear. In addition, incorrectly used or improperly preserving the live bacteria during the preparation process may cause pollution and expiration problems, which in turn may easily induce health risks; moreover, the composition of fermented milk is often used as the metabolic matrix of *Lactobacillus* and the use of flavoring and thus the ingredients often contain additives such as sugar, which may not be the best choice for the users who may have other complications (e.g. diabetes) or wish to control calorie intake.

At present, the patents of probiotics used for lowering blood pressure are mainly focused on the way that the live bacteria are given to fermented milk and the addition effect of the combination of several *Lactobacillus* strains is usually required. Relevant patents are briefly described as follows.

TW 201305331 and CN 102098923A disclosed that *Lactobacillus helveticus* can produce fermented products VPP (Valine-Proline-Proline) and IPP (Isoleucine-Proline-Proline) in animal milk via metabolism to inhibit ACE and be used for lowering blood pressure agent; this invention draws a conclusion that the fermented milks can be used for lowering blood pressure by inferring that VPP and IPP are reported to have the ability to inhibit ACE. TW 200603741 disclosed a method for preparing functional fermented milk containing ACE inhibitors. The procedure involves inoculating a suitable amount of *Lactobacillus* in raw milk for the preparation of fermented milk and said *Lactobacillus* is selected from the group consisting of *Lactobacillus* spp., *Streptococcus* spp. and *Bifidobacterium* spp. and said *Lactobacillus* produces ACE inhibitory peptides via fermented milk, which has been proved to be effective in lowering blood pressure by animal experiments in mouse.

Although related inventions have been proposed to probiotics as a way to lower blood pressure, because that pathway belongs to health food rather than pharmaceuticals, there is few human clinical data support. If a specific efficacy is required, the amount of bacteria needs considerable requirements. To achieve the indicated effect, a higher level of bacteria is required and the combined use of bacteria and ACE inhibitory peptide and live bacteria form is also necessary for fermented milk. In addition, except for *L. helveticus*, there is no related human clinical research that indicates that ingestion of a single strain of living bacteria can regulate human blood pressure; likewise, the previous study on *L. helveticus* also showed the fermented milk must be used in the form of living bacteria and combined with the mechanism of inhibiting the ACE inhibitory peptide to achieve the effect of lowering blood pressure. Further, because fermented milk also has the risks of living bacteria preservation and pollution, and adding ingredients usually contain sugar, for those who cannot take extra sugar or need to control their calorie intake, which is still not a feasible scheme.

SUMMARY OF THE INVENTION

To solve the above problems, the invention proposes a composition made from *Lactobacillus reuteri* GMNL-263 (*L. reuteri* GMNL-263) in probiotics to prevent or improve hypertension.

The invention achieves the effect of lowering blood pressure by sterilizing *L. reuteri* GMNL-263 through heat and becoming the form of dead bacteria. It is also found that the mechanism is different from the previous inhibition of ACE by inhibiting the proinflammatory cytokines and enhancing the expression of the *Bifidobacterium* in the probiotic group. This invention has been further proved by parallel comparison that even the same *Lactobacillus reuteri* strain belonging to different bacterial colonies (such as *L. reuteri* GMNL-89) cannot achieve the effect of lowering blood pressure.

The invention is a *Lactobacillus* composition belonging to probiotics, therefore it is safe and without the side effects of drugs and can be applied to prevent and treat hypertension. In addition, said invention is the first to disclose the form of the probiotic composition as dead bacteria and hence there is no limitation on ingestion. Unlike the previous probiotic compositions that need to be in the form of fermented milk to achieve the effect of lowering blood pressure, most importantly, diabetic patients or those who need to control their sugar intake can also use it safely, which becomes a great treatment for patients with complications. The invention is confirmed by clinical trials that the effect of GMNL-263 on lowering blood pressure is not commonly found in the same strain of *Lactobacillus reuteri* and hence whether the strain has the effect of lowering blood pressure needs to be confirmed via further tests. Unlike the mechanisms proposed in the prior arts, this invention first discloses that probiotics can lower blood pressure by inhibiting IL-1β and enhancing the expression of *Bifidobacterium*.

DETAILED DESCRIPTION OF THE INVENTION

The invention is exemplified by the following embodiments but is not limited by thereof. The materials used in the invention, unless specified otherwise, are all commercially available materials in the market and *Lactobacillus reuteri* GMNL-263 [here in after referred to as GMNL-263] is deposited China Center for Type Culture Collection (CCTCC) located at Wuhan University, Wuhan 430072 P.R. China on Nov. 13, 2009, with accession number of CCTCC M 209263.

Embodiment 1: Heat-Killed Dead GMNL-263 has the Effect of Lowering Blood Pressure This embodiment is a human clinical trial. Due to the fact that patients with type 2 diabetes mellitus (T2DM) have high risk for hypertension, so patients are diagnosed with type 2 diabetes for more than 6 months and the other inclusion criteria include: 7%<HbA1c (glycated hemoglobin)≤10%; age: 25~70 years; BMI>18.5; the exclusion criteria are:

pregnancy/pregnant women; with a serious disease during past 3 years, such as cancer (except for well-controlled benign tumor), kidney failure/dialysis, heart disease, stroke, autoimmune disease and ingestion of health foods except for hypoglycemic drugs for improving blood sugar level 4 weeks before and during the trial period, fixed edible probiotic product and fixed use of antibiotics, as well as liver/kidney abnormalities, poor gastrointestinal function and those who cannot take oral medications.

Figure 1A:
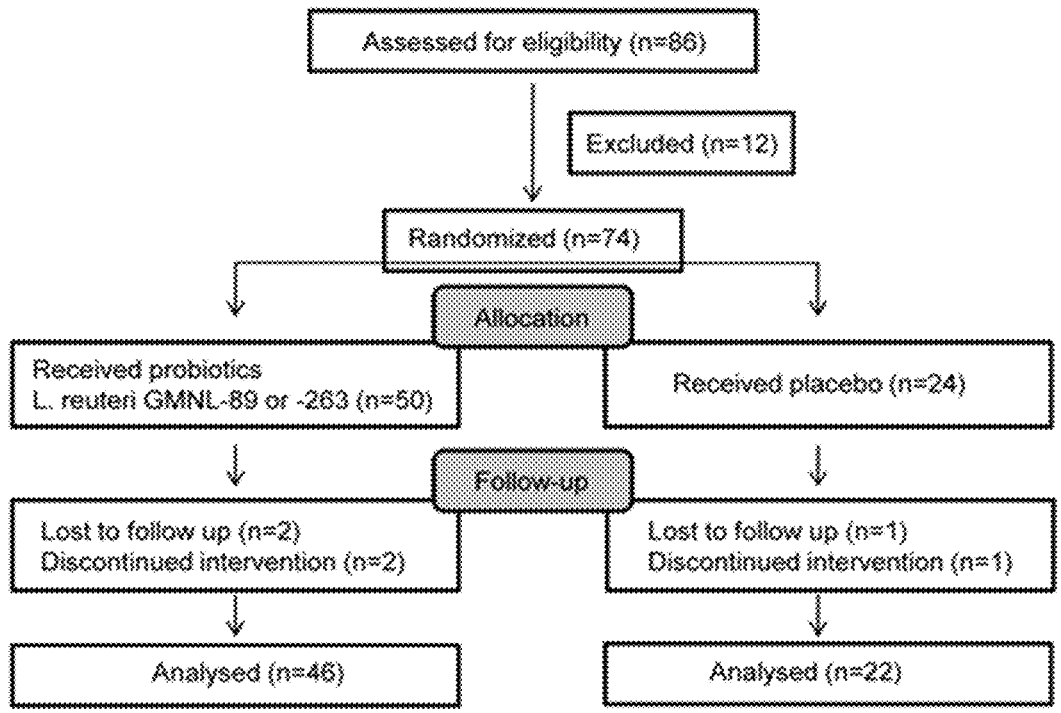
FIG. 1A shows the groups in the clinical trial.
Figure 1B:
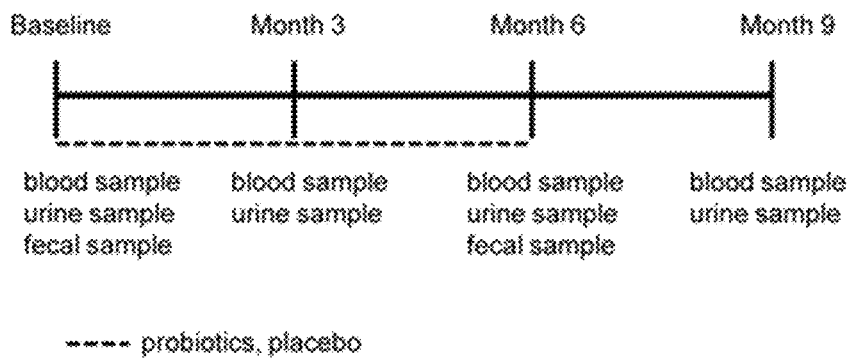
FIG. 1B shows the steps of the clinical trial.

The Clinical Trial Registration Number of this embodiment is NCT02274272 on Clinicaltrial.gov and was conducted in Changhua Christian Hospital; the Institutional Review Board (IRB) No. is 140703. FIG. 1A and FIG. 1B illustrate the groups and the process of the trail, which is a parallel research having a control group and using a double-blind and randomized allocation method that includes 74 subjects enrolled and divided into three groups randomly. After deducting the number of subjects leaving the trial, the total number of final analysis data was 68 subjects which includes the placebo group (N=22) and two probiotic trial groups: live *L. reuteri* GMNL-89 group (here in after referred to as GMNL-89) (N=22) and heat-killed dead *L. reuteri* GMNL-263 group (here in after referred to as GMNL-263) (N=24); in addition, after elimination of one subject who lost the fecal sample, the fecal samples of 67 subjects were analyzed based on their bacterial flora and the metabolic indicators such as baseline characteristics, blood sugar values, intestinal flora and proinflammatory cytokines before ingestion, 6 months after ingestion and 3 months after stopping using the probiotic product, that under the condition of concomitant use of current prescriptions.

The powder of live GMNL-89 bacteria and heat-killed dead GMNL-263 were prepared by GenMont biotech Incorporation via fermentation, the dose of live GMNL-89 was $4\times10^9$ cfu (colony forming unit)/day and the dose of dead GMNL-263 was $2\times10^{10}$ cells/day, the powder was given every day for a total of 6 months.

In the various statistical analyses, the comparison of the basic information was analyzed with Chi-square test or two-sample t-test, while the medication records and hypertension comparison were analyzed with Fisher exact test and the others use two-sample t-test.

First, the basic data of subjects were analyzed. Table 1 showed that there was no significant difference among the three groups of subjects at the beginning of the trial. Table 2 showed no significant difference in the proportion of hypertension among the three groups of subjects, indicating that the background conditions of the three groups of subjects were similar. Further, in terms of blood pressure, although these subjects all used drugs to control their blood pressure during the trial period, there were no statistical difference in the type of drugs used in the three groups. Therefore, there was no possibility of drug induced experimental error, but the systolic blood pressure (SBP) of all groups is still relatively high, indicating poor blood pressure control.

TABLE 1

Basic information of the three groups of subjects

| Baseline | placebo N = 22 | GMNL-263 N = 24 | P-value | GMNL-89 N = 22 | P-value |
|---|---|---|---|---|---|
| Male | 13 (59.1%) | 13 (54.2%) | 0.7365 | 12 (54.5%) | 0.7609 |
| Female | 9 (40.9%) | 11 (45.8%) | | 10 (45.5%) | |
| Age | 55.7 ± 8.55 | 53.88 ± 7.78 | 0.4346 | 53.32 ± 10.2 | 0.2302 |
| Height (cm) | 161.8 ± 7.28 | 162 ± 7.83 | 0.9176 | 163 ± 7.92 | 0.6173 |
| Weight (kg) | 72.4 ± 11.64 | 73.77 ± 12.54 | 0.7043 | 74.97 ± 15.73 | 0.5408 |
| BMI (kg/m2) | 27.53 ± 3.15 | 28.03 ± 3.88 | 0.6374 | 28.04 ± 4.29 | 0.6587 |
| SBP (mmHg) | 126.8 ± 9.93 | 132.9 ± 16.93 | 0.1378 | 126.2 ± 13.08 | 0.8668 |
| DBP (mmHg) | 75.32 ± 9.09 | 76.08 ± 6.93 | 0.7484 | 76.68 ± 8.87 | 0.6172 |
| Waist circumference (cm) | 95.45 ± 10.59 | 96.19 ± 9 | 0.7998 | 95.94 ± 12 | 0.8873 |
| Hip circumference (cm) | 100 ± 7.66 | 101.1 ± 7.95 | 0.6476 | 101.9 ± 10.86 | 0.5073 |
| GOT (U/L) | 31.73 ± 14.65 | 32.38 ± 17.84 | 0.8941 | 30.91 ± 10.39 | 0.8319 |
| GPT (U/L) | 39.59 ± 23.11 | 43.71 ± 27.67 | 0.5885 | 38.77 ± 15.88 | 0.8918 |
| HbA1c (%) | 7.91 ± 0.62 | 8.07 ± 0.67 | 0.4252 | 7.91 ± 0.68 | >0.999 |

TABLE 2

History of disease and drug use records of the three groups of subjects

| Variable | placebo N = 22 | GMNL-263 N = 24 | P-value | GMNL-89 N = 22 | P-value |
|---|---|---|---|---|---|
| Medical History (N) | | | | | |
| Hypercholesterolemia | 18 (81.8%) | 22 (91.7%) | 0.41 | 18 (81.8%) | >0.99 |
| Hypertension | 16 (72.7%) | 17 (70.8%) | >0.99 | 18 (81.8%) | 0.72 |
| Medication for Hypertension (N) | N = 22 | N = 24 | P-value | N = 22 | P-value |
| Diuretics | 6 (27.3%) | 8 (33%) | 0.75 | 4 (18.2%) | 0.72 |
| Beta-blockers | 6 (27.3%) | 9 (37.5%) | 0.54 | 7 (31.8%) | >0.99 |
| Alpha/Beta-blockers | 0 (0.0%) | 0 (0.0%) | NA | 1 (4.6%) | >0.99 |

TABLE 2-continued

History of disease and drug use records of the three groups of subjects

| | | | | | |
|---|---|---|---|---|---|
| Angiotensin-Converting Enzyme Inhibitor (ACEI) | 0 (0.0%) | 1 (4.2%) | >0.99 | 0 (0.0%) | NA |
| Angiotensin II Receptor Antagonist (AII RA) | 13 (59.1%) | 9 (37.5%) | 0.24 | 8 (36.4 %) | 0.23 |
| Calcium channel blockers (CCB) | 1 (4.6%) | 1 (4.2%) | >0.99 | 1 (4.6%) | >0.99 |
| Vasodilator | 2 (9.1%) | 3 (12.5%) | >0.99 | 0 (0.0%) | 0.49 |
| Mixed-Drug | 6 (27.3%) | 9 (37.5%) | 0.54 | 11 (50.0) | 0.22 |

| | placebo | GMNL-263 | | GMNL-89 | |
|---|---|---|---|---|---|
| Medication for Diabetes (N) | N = 22 | N = 24 | P-value | N = 22 | P-value |
| Insulin | 5 (22.7%) | 5 (20.8%) | >0.99 | 3 (13.6%) | 0.7 |
| Metformin | 20 (90.9%) | 22 (91.7%) | >0.99 | 20 (90.9%) | >0.99 |
| Sulphonylurea | 16 (72.7%) | 18 (75.0%) | >0.99 | 14 (63.6%) | 0.75 |
| DDP-4 inhibitor | | | | | |
| Sitagliptin | 4 (18.2%) | 2 (8.3%) | 0.41 | 2 (9.1%) | 0.66 |
| Vidagliptin | 2 (9.1%) | 2 (8.3%) | >0.99 | 3 (13.6%) | >0.99 |
| Saxagliptin | 12 (54.6%) | 10 (41.7%) | 0.56 | 9 (40.9%) | 0.55 |
| Linagliptin | 7 (31.8%) | 8 (33.3%) | >0.99 | 5 (22.7%) | 0.74 |
| GLP-1 Receptor agonists | | | | | |
| Exenatide | 0 (0.0%) | 2 (8.3%) | 0.49 | 1 (4.6%) | >0.99 |
| Liraglutide | 0 (0.0%) | 2 (8.3%) | 0.49 | 3 (13.6%) | 0.23 |
| Acarbose | 6 (27.3%) | 2 (8.3%) | 0.13 | 5 (22.7%) | >0.99 |

The results showed that after 6 months, the net change of glycosylated hemoglobin A1c (HbA1c) in the diabetic subjects taking the live GMNL-89 (i.e., net change=the value of the sixth month deducts that of the first month=6M-0M) was significantly reduced ($-0.39\pm0.80$, $P<0.05$), while the heat-killed dead GMNL-263 group was not significantly different from the placebo group ($0.24\pm0.93$), indicating that taking the heat-killed dead GMNL-263 does not affect the glycemic value of the diabetic subjects.

In terms of blood pressure (see Table 3), the net change of the systolic blood pressure (SBP) and the mean blood pressure of the heat-killed dead GMNL-263 group were decreased and showed significant statistical difference ($P<0.05$), indicating that GMNL-263 had the effect of lowering blood pressure. However, there was no significant change in the blood pressure values of the GMNL-89, same as *Lactobacillus reuteri* strain, indicating that GMNL-89 did not have the effect of regulating blood pressure. The comparison results also indicate that the effect of lowering blood pressure on the specific bacterial colonies of the *Lactobacillus reuteri* strain is not common and easy to be known, and it must be confirmed by experiments.

According to the results of clinical-biochemical data of the subjects after 3-month or 6-month of *L. reuteri* consumption (see Table 4), there was no significant net change in HbA1c (glycated hemoglobin) level at any time points in the heat-killed dead GMNL-263 group. The net changes in insulin, HOMA-IR, and fasting blood glucose (glucose-AC) among groups were not significant in comparison with those in the placebo group (Table 4). For other metabolic markers, a trend in decreasing blood lipid level was observed in the live *L. reuteri* GMNL-89 group. However, it is worth noting that there was no significant change in the blood lipid level of the heat-killed dead GMNL-263 group while the significant reductions in systolic blood pressure (SBP) and mean blood pressure (MBP) were observed (Table 4, p=0.0248 for SBP and p=0.0254 for mean pressure) after 6-months of intervention.

TABLE 3

Net blood pressure changes of the three groups of subjects after 6-month of trial

| | | placebo | GMNL-263 | | GMNL-89 | |
|---|---|---|---|---|---|---|
| | | N = 22 | N = 24 | P-value | N = 22 | P-value |
| SBP (mmHg) | 6 M – 0 M | 1.95 ± 13.93 | −7.54 ± 13.77 | 0.0248* | −2.62 ± 11.03 | 0.2146 |
| DBP (mmHg) | 6 M – 0 M | 0.36 ± 8.28 | −3.17 ± 5.45 | 0.0921 | −0.91 ± 6.71 | 0.5783 |
| pulse pressure (mmHg) | 6 M – 0 M | 1.59 ± 11.68 | −4.38 ± 12.54 | 0.1019 | −1.91 ± 8.69 | 0.2664 |
| mean pressure (mmHg) | 6 M – 0 M | 0.89 ± 8.95 | −4.63 ± 6.94 | 0.0254* | −1.55 ± 7.34 | 0.3285 |

TABLE 4

Clinical-biochemical data of the subjects after 3-month or 6-month of *L. reuteri* consumption.

| | | placebo[a] N = 22 | GMNL-263[a] N = 24 | P-value[b] | GMNL-89[a] N = 22 | P-value[b] |
|---|---|---|---|---|---|---|
| HbA1c (%) | 3 M-0 M | 0.22 ± 0.93 | 0.07 ± 0.67 | 0.5509 | −0.35 ± 0.74 | 0.0321 |
| | 6 M-0 M | 0.22 ± 0.87 | 0.24 ± 0.93 | 0.9427 | −0.39 ± 0.80 | 0.0212 |
| Insulin (mU/L) | 3 M-0 M | 8.00 ± 36.76 | 4.45 ± 21.24 | 0.6944 | −4.15 ± 17.86 | 0.1731 |
| | 6 M-0 M | 1.70 ± 9.08 | 16.25 ± 43.90 | 0.1249 | −3.14 ± 11.46 | 0.1282 |
| HOMA-IR | 3 M-0 M | 0.14 ± 5.57 | 0.03 ± 9.27 | 0.9605 | −1.83 ± 8.01 | 0.3500 |
| | 6 M-0 M | −0.12 ± 4.16 | 6.57 ± 19.17 | 0.1079 | −0.91 ± 5.82 | 0.6082 |
| Glucose AC (mg/dl) | 3 M-0 M | −9.36 ± 45.86 | −11.20 ± 53.96 | 0.9038 | −1.36 ± 22.53 | 0.4683 |
| | 6 M-0 M | −10.40 ± 53.00 | −9.38 ± 58.45 | 0.9525 | −0.32 ± 31.92 | 0.4515 |
| LDL (mg/dl) | 3 M-0 M | 3.73 ± 24.30 | 8.58 ± 14.82 | 0.4239 | −8.18 ± 17.47 | 0.0690 |
| | 6 M-0 M | −5.09 ± 25.13 | 1.79 ± 24.32 | 0.3505 | −4.50 ± 16.29 | 0.9267 |
| HDL (mg/dl) | 3 M-0 M | 1.18 ± 7.58 | −0.25 ± 5.19 | 0.4552 | −1.45 ± 9.50 | 0.3145 |
| | 6 M-0 M | −0.91 ± 9.73 | −1.67 ± 5.45 | 0.7497 | 0.32 ± 6.61 | 0.6272 |
| TG (mg/dl) | 3 M-0 M | 2.68 ± 96.38 | 8.71 ± 55.45 | 0.7989 | −12.30 ± 81.99 | 0.5823 |
| | 6 M-0 M | 22.18 ± 92.62 | 61.63 ± 213.90 | 0.4165 | −22.70 ± 68.88 | 0.0754 |
| CHOL (mg/dl) | 3 M-0 M | 4.77 ± 23.97 | 9.04 ± 19.46 | 0.5091 | −9.86 ± 23.40 | 0.0467 |
| | 6 M-0 M | −1.55 ± 25.34 | 8.17 ± 40.99 | 0.3355 | −4.45 ± 20.94 | 0.6802 |
| FFA (mmol/L) | 3 M-0 M | −0.04 ± 0.50 | −0.13 ± 0.51 | 0.5287 | −0.28 ± 0.41 | 0.0935 |
| | 6 M-0 M | 0.15 ± 0.61 | 0.02 ± 0.56 | 0.4540 | −0.15 ± 0.46 | 0.0712 |
| SBP (mmHg) | 3 M-0 M | −0.09 ± 15.06 | −6.33 ± 14.96 | 0.1659 | −4.55 ± 14.00 | 0.3155 |
| | 6 M-0 M | 1.95 ± 13.93 | −7.54 ± 13.77 | 0.0248 | −2.82 ± 11.03 | 0.2146 |
| DBP (mmHg) | 3 M-0 M | −0.59 ± 9.59 | −3.33 ± 5.79 | 0.2537 | −2.77 ± 9.55 | 0.4537 |
| | 6 M-0 M | 0.36 ± 8.28 | −3.17 ± 5.45 | 0.0921 | −0.91 ± 6.71 | 0.5783 |
| pulse pressure (mmHg) | 3 M-0 M | 0.5 ± 11.08 | −3 ± 11.71 | 0.3034 | −1.77 ± 9.23 | 0.4641 |
| | 6 M-0 M | 1.59 ± 11.68 | −4.38 ± 12.54 | 0.1019 | −1.91 ± 8.69 | 0.2664 |
| mean pressure (mmHg) | 3 M-0 M | −0.42 ± 10.47 | −4.33 ± 8.16 | 0.1682 | −3.36 ± 10.35 | 0.3545 |
| | 6 M-0 M | 0.89 ± 8.95 | −4.63 ± 6.94 | 0.0254 | −1.55 ± 7.34 | 0.3285 |

Abbreviations:
HbA1c, glycated hemoglobin;
HOMA-IR, homeostatic model assessment-insulin resistance;
LDL, low-density lipoprotein;
HDL, high-density lipoprotein;
TG, triglycerides;
CHOL, cholesterol;
FFA, free fatty acid;
SBP, systolic blood pressure;
DBP, diastolic blood pressure;
PP, pulse pressure;
MBP, mean blood pressure.
[a]Data were calculated by the value of later time point (3 month (3 M) or 6 month (6 M)) minus to starting point (0 M) and presented as mean ± SD.
[b]Two sample t-test analysis was used to compare mean values between placebo and heat-killed dead GMNL-263 or live GMNL-89 groups.

Embodiment 2: Heat-Killed Dead GMNL-263 Shows the Effect of Lowering Blood Pressure by Reducing the Proinflammatory Cytokine IL-1β

To examine which mechanism of GMNL-263 is mediated to the effect of lowering blood pressure, further changes in cytokine levels were analyzed. First, the blood samples of the subjects in three groups were collected at the beginning of trial (OM) and 6 months later (6M) and ELISA kits were used to analyze the content of various cytokines, including human IL-6 (Cat #900-K16, PeproTech, USA), human IL-10 (Cat #900-K21, PeproTech, USA), human TNF-α (Cat #50-114-2609, eBioscience, USA) and human IL-1β (Cat #437005, Biolegend, USA); the data processing is the net change value obtained from the value of the sixth month (6M) deducting the initial value (OM), and further statistical analysis is carried out with two-sample t-test.

The results indicate that after taking GMNL-263 for 6 months, the IL-1β in subjects' blood showed a significant decrease in statistical significance when compared with the placebo group, whereas no significant differences of the other cytokines were observed between the two groups (see Table 5), indicating that GMNL-263 was regulated by the decline of IL-1β to adjust the chronic inflammation reaction of the whole body, which in turn achieves the goal of lowering blood pressure.

TABLE 5

Changes of cytokines in the blood of the three groups of subjects after 6 months of trial

| | | placebo N = 22 | GMNL-263 N = 24 | P-value | GMNL-89 N = 22 | P-value |
|---|---|---|---|---|---|---|
| IL-1β (pg/ml) | 6 M − 0 M | 0.21 ± 1.52 | −1.43 ± 2.7 | 0.0181* | −0.72 ± 1.94 | 0.1027 |
| IL-6 (ng/ml) | 6 M − 0 M | 0.9 ± 1.8 | 1.55 ± 2.41 | 0.3189 | 0.95 ± 2.65 | 0.9461 |
| IL-10 (ng/ml) | 6 M − 0 M | 1.04 ± 2.41 | 2.05 ± 3.25 | 0.2469 | 1.48 ± 3.09 | 0.6109 |
| TNF-α (pg/ml) | 6 M − 0 M | −3.07 ± 72.22 | 12.81 ± 86 | 0.5191 | −32 ± 81.24 | 0.2317 |

Embodiment 3: Heat-Killed Dead GMNL-263 has the Effect of Lowering Blood Pressure by Enhancement of the Expression of *Bifidobacterium*

To clarify whether the effect of GMNL-263 on lowering blood pressure is related to the regulation of intestinal probiotics, the fecal samples were collected from the subjects at the beginning (OM) and the sixth month (6M) of the trial to analyze the DNA of the stool flora by using quantitative polymerase chain reaction (Q-PCR) and calculate the changes of the flora after taking the probiotics for 6 months. The calculation method is: (the CT [Threshold cycle] value of the fecal DNA after taking the probiotics for 6 months obtained by the Q-PCR—the CT value of the total bacteria)=, ΔCt, ΔCt −(the CT value of the fecal DNA collected from those who have not taken the probiotics obtained by the Q-PCR— the CT value of the total bacteria)= ΔΔCt, which is converted to $2^{-\Delta\Delta Ct}$ that is the change of the flora after taking the probiotics for 6 months.

The analysis of stool flora by the Q-PCR can be divided into two parts: DNA extraction and the Q-PCR analysis. First, the Q1Aamp DNA Stool Mini Kit (QIAGEN, Lot. 51504) was used for extraction of DNA from fecal samples, the RNA later was removed from the patient's stool before Buffer ASL was added and the sample was then placed on a heat plate for heating at 70° C. for 5 minutes; next, added to the 0.1 mm sterilized microbeads (Model No.:BioSpec Products 0.1 MM ZIRCONIA/SILICA BEADS, Cat. No. 11079101z) and vortexed strongly for at least 15 seconds until the stool was mixed and crushed homogenously; the sample was then subjected to centrifugation at 13,000 rpm for 1 minute, the supernatant was collected for DNA extraction and the concentration of the extracted DNA was adjusted to 1 ng/μl for future use.

Next, the Q-PCR analysis of the stool was carried out. The above extracted DNA was used as a template for the Q-PCR and each reagent with 5 μl was added to the 2× Rotor-Gene SYBR Green PCR Master Mix (QIAGEN, Cat. 204076), 2 μl of the fecal DNA was added before addition of 3 μl of the flora primers (0.66 μM Forward (F)+Reverse primers (R)) to make up the total volume to 10 μl and the Q-PCR is executed by the PCR machine (Model No. QIAGEN: Rotor-Gene Q 2Plex).

The data statistical analysis of the flora changes was carried out by using the two-sample t-test and the correlation analysis between the changes of the flora and blood pressure was carried out by using PASW Statistics 18 Software (SPSS Inc.) for conducting Spearman's rho correlation.

Figure 2:
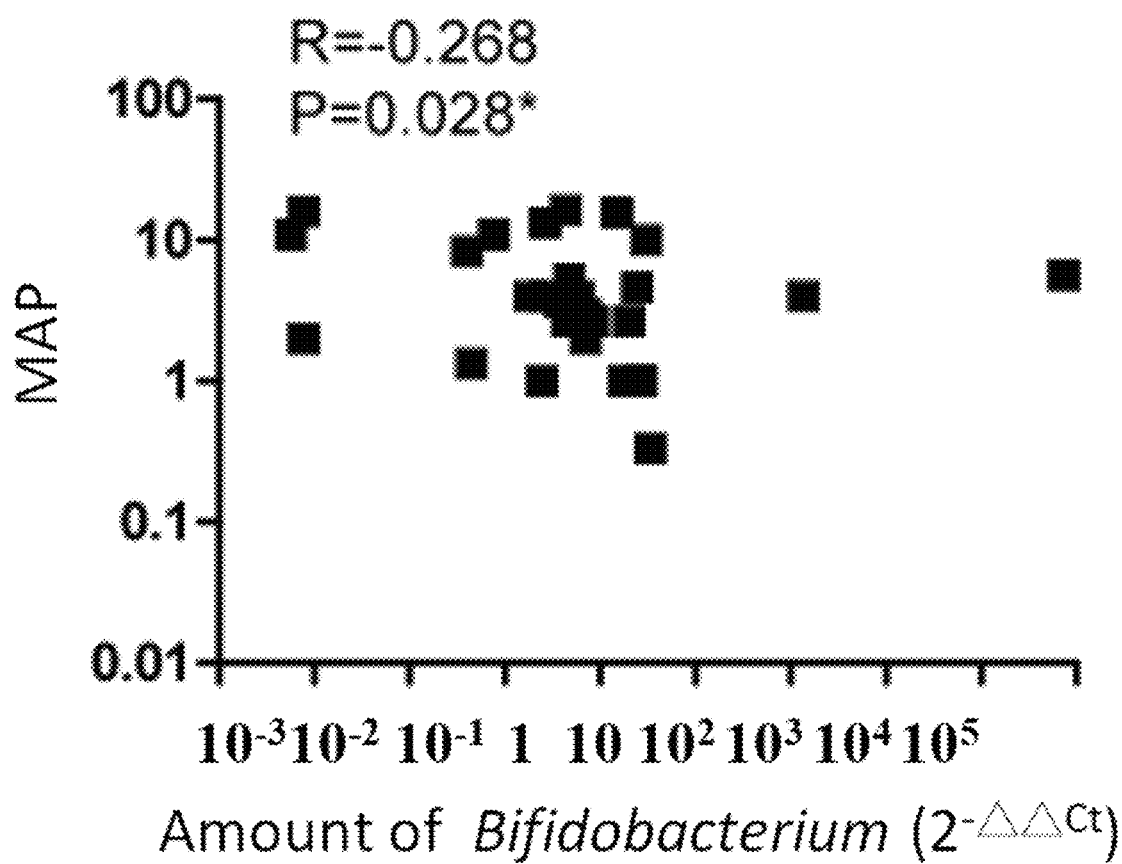
FIG. 2 shows the relevance analysis of the mean arterial pressure (MAP) and probiotic strains of *Bifidobacterium*.

The results indicate that after the subjects taking the heat-killed dead GMNL-263 for 6 months, the expression of *Bifidobacterium* in the probiotics group of these subjects increased and showed a statistically significant difference as compared with the placebo group (see Table 6). In order to clarify the correlation between the changes of flora and blood pressure, by further utilization of correlation statistical analysis, it was found that the increasing amount of *Bifidobacterium* was negatively correlated with the net change of the mean blood pressure (R=−0.268; P=0.028, see FIG. 2), indicating that blood pressure will be reduced when the amount of *Bifidobacterium* increases. Therefore, the result proves that heat-killed dead GMNL-263 can achieve the effect of lowering blood pressure by increasing the *Bifidobacterium* in the feces of the probiotics.

TABLE 6

Microbiological changes of the three groups of subjects after 6 months of trial

| Microbiota | | placebo | GMNL-263 | P-value | GMNL-89 | P-value |
|---|---|---|---|---|---|---|
| *Lactobacillu_reuteri* | 6 M – 0 M | 1.53 ± 1.77 | 6.23 ± 11.25 | 0.0548 | 98.43 ± 174.3 | 0.0165* |
| *Lactobacillus* | 6 M – 0 M | 2.51 ± 3.66 | 14.53 ± 52.73 | 0.2767 | 5.47 ± 20.02 | 0.5025 |
| *Bifidobacterium* | 6 M – 0 M | 6.28 ± 19.74 | 73.72 ± 156.2 | 0.04868* | 3441 ± 15649 | 0.3149 |
| *Akkermansia muciniphila* | 6 M – 0 M | 25.84 ± 59.38 | 170 ± 815.3 | 0.3953 | 81.07 ± 265.2 | 0.3559 |
| *Clostridium* cluster I | 6 M – 0 M | 20.43 ± 81.26 | 5.57 ± 10.21 | 0.4149 | 2.21 ± 2.78 | 0.3167 |
| Bacteroidetes | 6 M – 0 M | 1.42 ± 1.29 | 2.47 ± 3.53 | 0.18 | 7.21 ± 24.39 | 0.28 |
| Firmicutes | 6 M – 0 M | 1.57 ± 2.71 | 3.02 ± 3.35 | 0.12 | 1.62 ± 1.73 | 0.94 |
| Bacteroidetes/Firmicutes | 6 M – 0 M | −99.37 ± 338.03 | −87.98 ± 213.26 | 0.9 | 22.28 ± 165.75 | 0.15 |

The present invention has proved that after taking the heat-killed dead *Lactobacillus reuteri* GMNL-263 for 6 months can help the diabetic patients with hypertension symptoms reduce systolic blood pressure and mean blood pressure without affecting blood glucose values, which is beneficial to diabetic patients who need to control sugar or calorie intake. The *L. reuteri* GMNL-263 is subjected to heat sterilized treatment and can be prepared to products such as capsules or powder packs and has the advantages of high stability and convenience; in addition, because *Lactobacillus* is the probiotic bacteria and is considered as health food and thus safety is not a concern. Common people can use this product to prevent or control hypertension and there is no population limitation and thus the product can be used in many ways. The present invention further verified by correlation statistical analysis that heat-killed dead *L. reuteri* GMNL-263 can achieve the effect of lowering blood pressure simultaneously by reducing the proinflammatory cytokine IL-1P and regulating intestinal flora of the patients to increase *Bifidobacterium* of the probiotics. Furthermore, by using the same species of GMNL-89 as the control group, the results proved that not all *L. reuteri* can be used for lowering blood pressure, but only requires specific strains and should be confirmed by clinical trials. The *L. reuteri* GMNL-263 of the present invention is the first disclosure of using probiotics in the field of improving hypertension application, which breaks through the using forms and population limitation of the prior arts.

What is claimed is:

1. A method for treating hypertension in an individual, comprising administering to the individual a composition comprising a therapeutically effective amount of *Lactobacillus reuteri* GMNL-263 with the deposition number CCTCC M209263; wherein the individual suffers from hypertension; wherein the therapeutically effective amount is $2\times10^{10}$ CFUs of dead *Lactobacillus reuteri* GMNL-263 per day; wherein the therapeutically effective amount of $2\times10^{10}$ CFUs of dead *Lactobacillus reuteri* GMNL-263 does not significantly affect blood lipid levels of the individual, wherein the individual is not living with obesity.

2. The method as recited in claim 1, wherein the *Lactobacillus reuteri* GMNL-263 does not significantly affect glycated hemoglobin levels of the individual.

3. The method as recited in claim 1, wherein the composition inhibits the expression of a proinflammatory cytokine and enhances the growth of a probiotic in the individual.

4. The method as recited in claim 3, wherein the proinflammatory cytokine is IL-1β.

5. The method as recited in claim 3, wherein the probiotic is *Bifidobacterium*.

* * * * *